United States Patent [19]

Vandegriff

[11] Patent Number: 4,967,746

[45] Date of Patent: Nov. 6, 1990

[54] DUAL CHAMBER PACEMAKER WITH ADJUSTABLE BLANKING AND V-A EXTENSION

[75] Inventor: Joseph W. Vandegriff, Freeport, Tex.

[73] Assignee: Intermedics, Inc., Angleton, Tex.

[21] Appl. No.: 426,316

[22] Filed: Oct. 23, 1989

[51] Int. Cl.⁵ ............................................. A61N 1/00
[52] U.S. Cl. ............................................. 128/419 PG
[58] Field of Search ................................. 128/419 PG

[56] References Cited

U.S. PATENT DOCUMENTS

| | | | |
|---|---|---|---|
| 4,284,082 | 8/1981 | Funk et al. | 128/419 PG |
| 4,624,260 | 11/1986 | Baker, Jr. et al. | 128/419 PG |
| 4,825,870 | 5/1989 | Mann et al. | 128/419 PG |

*Primary Examiner*—Lee S. Cohen
*Assistant Examiner*—S. Getzow
*Attorney, Agent, or Firm*—John R. Merkling

[57] ABSTRACT

A dual chamber pacemaker with variable V-A delay based on detection of multiple criteria before lengthening the V-A delay period. Before the V-A delay period can be extended, the pacemaker must be stimulating the ventricle at a maximum ventricular rate, and an atrial event must be sensed in a relative atrial refractory period. During this interval the pacemaker would not respond to an atrial event that was sensed, but the occurrence of the event would be detected. To optimize a ventricular blanking period, in each cardiac cycle, the energy level of the atrial output pulse and the sensitivity of the ventricular sense amplifier are sampled. Based on these dynamic parameters, the duration of the ventricle blanking period is adjusted for each cycle so that a minimum ventricular blanking period can be maintained without cross-talk.

19 Claims, 5 Drawing Sheets

DUAL CHAMBER PACEMAKER WITH ADJUSTABLE BLANKING AND V-A EXTENSION

TECHNICAL FIELD

My invention relates to pacemakers which monitor the operation of the heart and stimulate heart tissue as required to maintain the proper operation of the heart. More particularly, the invention relates to a microprocessorcontrolled dual chamber pacemaker which limits atrial pacing during a Wenckebach pause and which also varies the ventricular pacemaking refractory period based on atrial pulse energy and/or ventricular sense amplifier gain.

BACKGROUND OF THE INVENTION

It has long been known that the heart muscle provides its pumping function in response to electrical events which occur in the atrium and ventricle of the heart. Conductive tissue connects the atrium and the ventricle and provides a path for the conduction of electrical signals between the two areas. In a normal heart, a natural atrial event spontaneously occurs in the atrium and a corresponding ventricular event occurs later in the ventricle after a time interval typically called the A-V interval. After the ventricular event a new atrial event occurs in the atrium to trigger a succeeding ventricular event. The synchronized electrical events occurring naturally in the atrium and ventricle cause the heart muscle to rhythmically expand and contract and thereby pump blood throughout the body.

In a diseased heart atrial and ventricular events may not naturally occur in the required synchronized manner and the pumping action of the heart is therefore irregular and ineffective to provide the required circulation of blood within the body. The required synchronized activity of such diseased hearts can be maintained by a pacemaker which applies synchronized stimulating pulse to either or both the atrium and the ventricle to pace the heart.

In the early stages of pacemaker development, pacemakers were employed to asynchronously stimulate the ventricle of the heart without regard to natural electrical activity occurring in either the atrium or the ventricle. Although this approach had the advantage of simplicity, there was considerable risk due to the fact that paced ventricular events could interact with natural ventricular events to cause the heart to go into a dangerous arrhythmia.

As the art of pacing advanced, pacemakers were provided with circuitry which sensed the occurrence of natural ventricular and atrial activity and paced the heart in either the atrium or ventricle only when required to maintain proper operation of the heart. A dual chamber pacemaker can operate in what is known as DDD mode, wherein electrical events are sensed in the atrium and ventricle and the atrium and ventricle are paced accordingly. Pacemakers may also be operated in VDD mode to sense electrical events in the atrium and ventricle but pace only in the ventricle. Other pacemaker modes of operation are employed to sense or pace in either the atrium or the ventricle, as required for the particular needs of a patient.

It has been found that pacemakers which operate in the DDD or VDD modes can, under certain circumstances, sustain a dangerous tachycardia condition. A pacemaker sustained tachycardia condition is defined as an operational pacing state wherein the pacemaker erroneously stimulates the ventricle of a heart at a dangerously high rate for sustained periods of time.

Pacemaker sustained tachycardia is initiated when a ventricular event occurs at a time during which the connective tissue between the atrium and ventricle can transmit retrograde electrical signals from the ventricle to the atrium. The conduction of the ventricular signal to the atrium may cause an atrial depolarization. The pacemaker senses this retrograde atrial signal and then paces the ventricle at an A-V time period following the signal. The paced ventricular signal is conducted to the atrium where it again causes an atrial depolarization. The pacemaker therefore continues to pace the ventricle at a relatively high rate defined by the sum of the A-V interval and the retrograde conduction time between the ventricle and atrium. This high rate may be sustained indefinitely by the pacemaker, because the retrograde condition ensures that the pacemaker detects what appear to be high rate atrial events and tracks these events by generating corresponding high rate ventricular paces. This pacemaker sustained tachycardia condition overstimulates the heart, at considerable danger to the patient.

One way of minimizing the impact of pacemaker sustained tachycardia is to provide a ventricular tracking limit for a maximum ventricular pacing rate. A pacemaker will not stimulate the ventricle faster than the maximum pacing rate. If such a limit is imposed, however, there can be a progressive loss of A-V synchrony or coordination between the atrial and ventricular chambers of the heart. For example, if the atrial rate is slightly faster than the ventricular tracking limit, then the sensed atrial event would be detected by the pacemaker earlier and earlier in each cardiac cycle. The time between ventricular pacing pulses would be constant, but the delay between a sensed atrial event and a ventricular pace would appear to lengthen in each cycle, since the maximum ventricular pacing rate would be the controlling parameter.

In a DDD pacer, sense amplifiers in the atrium and the ventricle are usually disabled during a pacing pulse, and for a selected period of time thereafter. This is called a pacemaker refractory period. For example, if a atrial event occurs during an atrial pacemaker refractory period, it will not be detected by a most pacemakers. When the pacer is stimulating the ventricle at its ventricular maximum pacing rate, if there is a sustained atrial tachycardia, the delay between the detected atrial event and the ventricular pace will become longer and longer until the atrial event falls within the atrial pacemaker refractory period caused by the ventricular pace of the preceding cycle. When the atrial event falls within the atrial pacemaker refractory period, it is not detected by the ordinary pacemaker. This causes the pacemaker to skip a ventricular beat after which atrial/ventricular synchrony is usually restored with the next properly sensed atrial event. This pause is referred to as Wenckebach behavior.

In DDD pacing, however, the pacemaker is programmed to stimulate the atrium, as well as the ventricle. If a atrial event is not detected, the pacemaker may improperly pace the atrium during the Wenckebach pause. Such an event could produce conditions to permit retrograde conduction to the atrium after the ventricular pacing pulse. Even if the atrial pacing pulse caused a contraction in the atrium, it would effectively accelerate the atrial rate, which is probably already faster than the ventricular tracking limit.

This atrial pace during the Wenckebach pause can sometimes be avoided by lengthening the V-A delay during the pause to give more time for the pacemaker to sense the events in the atrium. Whenever the ventricle is paced at the maximum pacing rate, the ventricle to atrium (V-A) delay, is lengthened by a predetermined value. This procedure is utilized by the assignee of the present invention in one of its marketed products, the Cosmos ® Pacemaker. This method is effective, but it has certain limitations. For example, if a premature atrial contraction occurs, it may cause a ventricular pace which is momentarily at the ventricular tracking limit. If instantaneous ventricular rate is the only criteria for lengthening the V-A delay period, the premature atrial contraction will cause an improper lengthening of the VA delay. In addition, sensing of atrial noise may cause the same response.

In dual chamber pacerkmakers, atrial paced events can be erronously sensed in the ventricle as well. This condition is known as "cross-talk", where events in one chamber interfere with the operation of the other chamber. If an atrial paced event is erroneously detected in the ventricle as a sensed event, the ventricular output of the pacemaker would be inhibited. The ventricle would not be paced by the pacemaker, and the patient's cardiac output could decline. To avoid this situation, pacemakers turn off or "blank" the sense amplifier in the ventricle during an atrial pulse and for a short time thereafter. This ventricular blanking period is a time when the condition of the ventricle will not be sensed by the pacemaker. The ventricular blanking period should be kept as short as possible so that all valid ventricular events will be sensed.

The duration of the ventricular blanking period has, in the past, been selected with reference to the energy level of the atrial output pulse, as set by the attending physician. More advanced pacemakers, however, are capable of dynamically adjusting both the energy level of the atrial output pulse and the sensitivity of the ventricular sense amplifier. Variations in both the atrial output pulse energy level and the ventricular sense amplifiers sensitivity affect the duration of the optimum ventricular blanking period.

SUMMARY OF THE INVENTION

I have discovered that improper lengthening of the V-A Delay can be avoided by detection of additional criteria before lengthening the V-A delay period. In my invention, before the V-A delay period can be extended, the pacemaker must be stimulating the ventricle at the maximum ventricular rate, and an atrial event must be sensed in part of the atrial pacemaker refractory period. During this interval, called a relative atrial refractory period, the pacemaker would not respond to a sensed atrial event, but the occurrence of the event would be recorded. If both conditions (maximum ventricular rate and detected atrial event during the relative atrial pacemaker refractory period) have occurred, the pacer would extend the VA delay, to allow more time for intrinsic atrial activity during the Wenckebach pause.

I have also invented a means for dynamically optimizing the ventricular blanking period. In each cardiac cycle, the energy level of the atrial output pulse and the sensitivity of the ventricular sense amplifier are sampled. Based on these dynamic parameters, the duration of the ventricular blanking period is adjusted for each cycle so that a minimum ventricular pacemaker blanking can be maintained without cross-talk.

With the forgoing in mind it is a principle object for my invention to provide a dual chamber pacemaker with means for avoiding improper sensing in one chamber of events in the other.

Another important object for my invention is to provide a dual chamber pacemaker which can maintain atrial/ventricular synchrony in Wenckebach behavior, by conditional sensing during a relative atrial pacemaker refractory period.

Another object of my invention is to provide dual chamber pacemaker which can dynamically adjust the ventricular blanking period.

It is also an object of my invention to provide a dual chamber pacemaker which can optimize the ventricular blanking period based on multiple parameters.

A further important object of my invention is to provide such a dual chamber pacemaker wherein the ventricular blanking period is adjusted with reference to multiple parameters dynamically set by the pacemaker.

Other objects and advantages of my invention will be apparent to those skilled in the art from the following detailed description and accompanying drawings.

DETAILED DESCRIPTION OF THE PRESENTLY PREFERRED EMBODIMENTS

Figure 1:
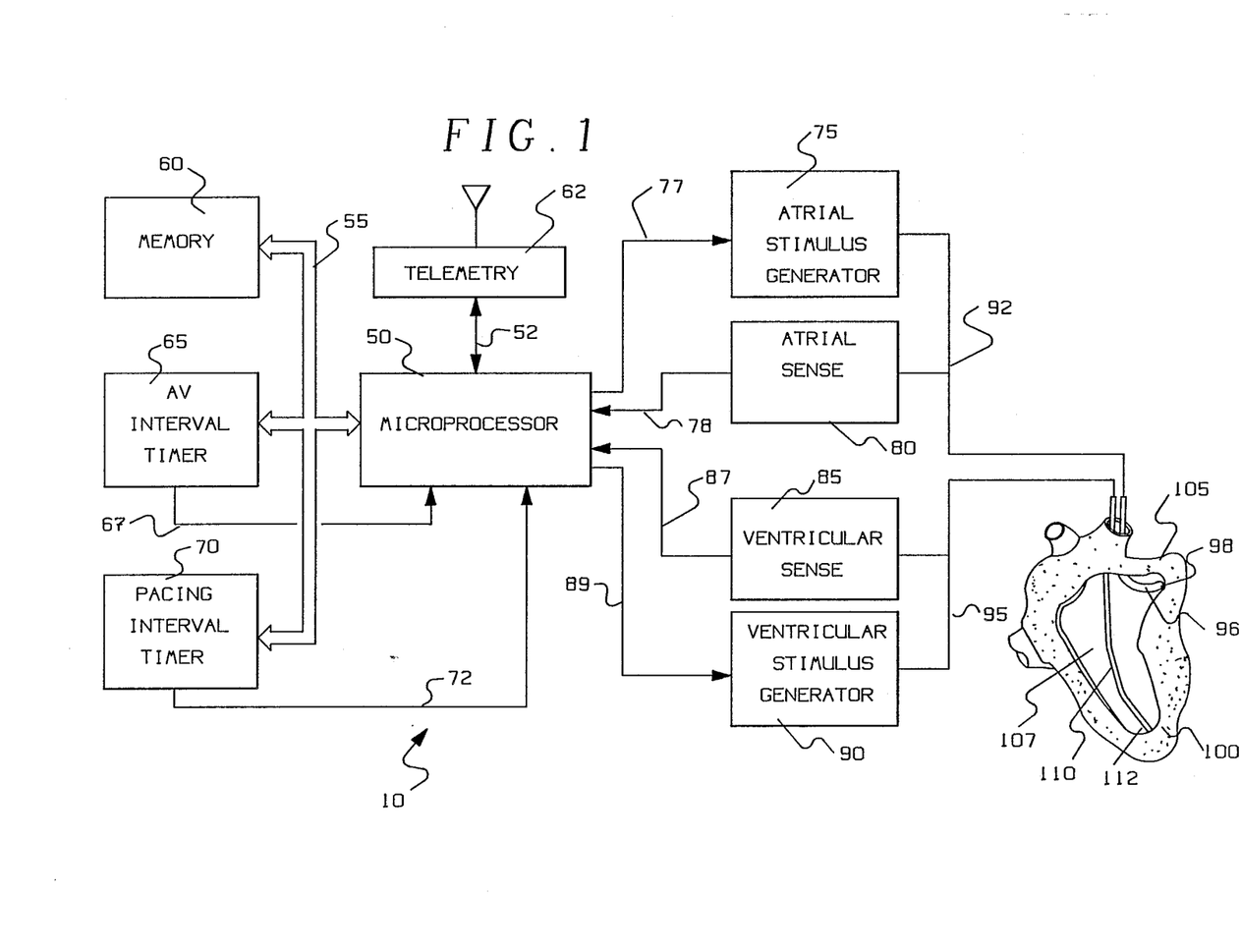
FIG. 1 is a block diagram of a pacemaker suitable for implantation of the present invention.

FIG. 1 is a block diagram illustrating a rate adaptive pacemaker 10 according to my invention. A microprocessor 50 preferably provides pacemaker control and computational facilities. It will be appreciated that other forms of circuitry, such as analog or discrete digital circuitry can be used in place of microprocessor 50. However, a microprocessor is preferred for its miniature size and its flexibility, both of which are of critical importance in the implantable systems in which it is envisioned the invention will find use. A particularly energy efficient microprocessor which is designed specifically for use herein is fully described in Gordon et al., U.S. Pat. No. 4,404,972, which is assigned to the assignee of application and the disclosure thereof is incorporated herein by reference.

The microprocessor 50 has input/output ports connected in a conventional manner via bidirectional bus 55 to memory 60, an A-V interval timer 65, and a pacing interval timer 70. In addition, the A-V interval timer 65 and pacing interval timer 70 each has an output connected individually to a corresponding input port of the microprocessor 50 by lines 67 and 72 respectively.

Memory 60 preferably includes both ROM and RAM. The microprocessor 50 may also contain additional ROM and RAM as described in the Gordon et al. U.S. Pat. No. 4,404,972. The pacemaker operating routine is stored in ROM. The RAM stores various programmable parameters and variables which are described in detail below in conjunction with the pacemaker operation.

The A-V and pacing interval timers 65 and 70 may be external to the microprocessor 50, as illustrated, or internal thereto, as described in the Gordon et al. U.S. Pat. No. 4,404,972. The timers 65 and 70 are suitably conventional up or down counters of the type that are initially loaded with a count value and count up to or down from the value and output a roll-over bit upon completing the programmed count. The initial count value is loaded into timer 65 and 70 on bus 55 and the respective roll-over bits are output to the microprocessor 50 on lines 67 and 72.

The microprocessor 50 preferably also has an input/output port connected to a telemetry interface 62 by line 52. The pacemaker when implanted is thus able to receive pacing and rate control parameters from an external programmer and send data to an external receiver if desired. Many suitable telemetry systems are known to those skilled in the art. One such system and encoding arrangement is described in Calfee et al. U.S. Pat. No. 4,539,992 which is also assigned to the assignee of my application. That description is incorporated herein by reference.

The microprocessor 50 output ports are connected to inputs of an atrial stimulus pulse generator 75 and a ventricle stimulus pulse generator 90 by control lines 77 and 89 respectively. The microprocessor 50 transmits pulse parameter data, such as amplitude and width, as well as enable/disable and pulse initiation codes to the generators 75 and 90 on the respective control lines.

The microprocessor 50 also has input ports connected to outputs of an atrial sense amplifier 80 and a ventricular sense amplifier 85 by lines 78 and 87 respectively. The atrial and ventricular sense amplifiers 80 and 85 detect occurrences of P-waves and R-waves respectively. The atrial sense amplifier 80 outputs a signal on line 78 to the microprocessor 50 when it detects a P-wave. This signal is latched to the microprocessor 50 input port by a conventional latch (not shown). The ventricle sense amplifier 85 outputs a signal on line 87 to the microprocessor 50 when it detects a R-wave. This signal is also latched to the microprocessor 50 input port by a conventional latch (not shown).

The input of the atrial sense amplifier 80 and the output of the atrial stimulus pulse generator 75 are connected to a first conductor 92, which is inserted in a first conventional lead 96. Lead 96 is inserted into the heart 100 intravenously or in any other suitable manner. The lead 96 has an electrically conductive pacing/sensing tip 98 at its distal end which is electrically connected to the conductor 92. The pacing/sensing tip 98 is preferably lodged in the right atrium 105.

The input of the ventricular sense amplifier 85 and the output of the ventricular stimulus pulse generator 90 are connected to a second conductor 95. The second conductor 95 is inserted in a second conventional lead 110 which is inserted intravenously or otherwise in the right ventricle 107 of the heart 100. The second lead 110 has an electrically conductive pacing/sensing tip 112 at its distal end. The pacing/sensing tip 112 is electrically connected to the conductor 95. The pacing/sensing tip 112 is preferably lodged on the wall of the right ventricle.

The conductors 92 and 95 conduct the stimulus pulses generated by the atrial and ventricular stimulus pulse generators 75 and 90, respectively to the pacing/sensing tips 98 and 112. The pacing/sensing tips 98 and 112 and corresponding conductors 92 and 95 also conduct sensed cardiac electrical signals in the right atrium appendage and right ventricle to the atrial and ventricular amplifiers 80 and 85 respectively.

The sense amplifiers 80, 85 enhance the electrical signals. In the preferred embodiments of my invention, the amplifiers 80, 85 have an automatic gain control feature, as described in copending U.S. patent application Ser. No. 07/203,493, for "Implantable Cardiac Stimulator with Automatic Gain Control" by Baker, Haluska and myself. That application is assigned to the same assignee as my present invention, and the disclosure thereof is incorporated herein by reference. Preferably, the sense amplifiers 80, 85 have a range of gain of on the order of a least 8:1. As will be explained in more detail below, AGC with bandpass filtering is employed to provide the function of reducing the amplitude of signals outside the frequency band of interest.

Figure 2:
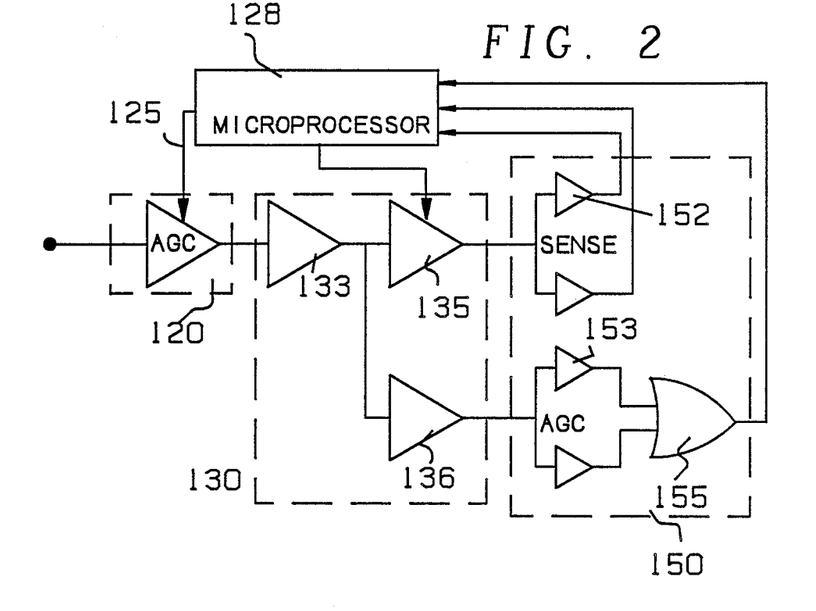
FIG. 2 is a schematic diagram of an automatic gain control circuit of the pacemaker of FIG. 1.

Sense amplifiers 80, 85 and their relationship to the microprocessor 50 are illustrated in greater detail in FIG. 2. The ECG waveform components detected by the sensing electrodes are applied to an AGC amplifier 120. The gain of amplifier 120 is automatically controlled by a feedback loop 125 containing a portion 128 of the microprocessor 50 (FIG.1). The signals processed by AGC amplifier 120 are further enhanced by a filter section 130 having a primary high gain bandpass amplifier 133 to amplify signals within a selected band. The output of amplifier 133 is split and applied to separate amplifiers 135 and 136, the former being digitally controlled by microprocessor portion 128. The output derived from amplifier and filter stages 120 and 130 is applied to a quad comparator 150, comprising a set of sensing target comparators 152 and a set of AGC target comparators 153, 155, which develop three inputs to the microprocessor 128 in the feedback loop.

The sensing target comparators 152 determines positive and negative sense threshold targets (see FIG. 3.) and the AGC target comparators 153, 155 set AGC target thresholds to determine the gain of AGC amplifier 120. A sensing margin is defined as the ratio of peak signal size at the inputs to sensing target comparators 152 and their respective sensing thresholds. A ratio greater than one must be chosen in order to avoid loss of sensing as a consequence of a reduction in signal amplitude. For example, the use of a 2-to-1 margin would mean that the signal amplitude would have to be reduced by one-half to lose sensing. The goal of the AGC system is to maintain a preset sensing margin. For a given threshold level on the sensing comparator, this may be achieved by adjusting the gain of the AGC amplifier 120 so that the peak voltage seen by the sensing comparators remains more or less constant. The microprocessor 128 samples the output of the AGC comparators 153, 155 on a cycle by cycle basis. In essence, if the waveform peak (see FIG. 3) exceeds the threshold of the AGC detector, the microprocessor 128 will reduce the gain a small amount. If the waveform peak does not exceed the threshold of the AGC detector, it will increase the gain a small amount.

Figure 3:
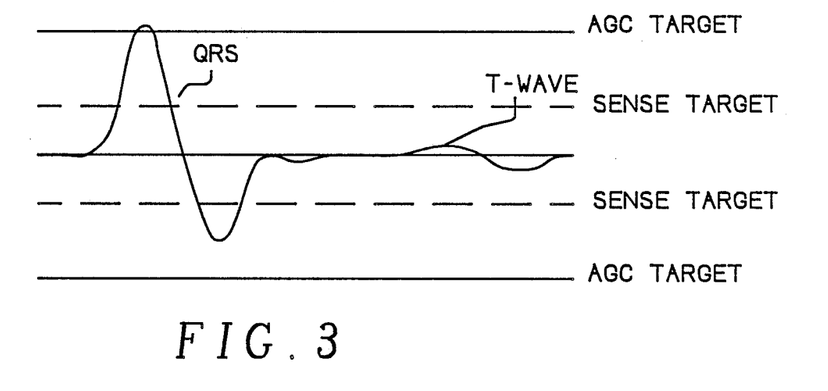
FIG. 3 is a waveform with reference to the circuit of FIG. 2.

In the presence of a QRS complex which is being monitored by the sense amplifier with its sensing and AGC targets, the microprocessor 128 seeks to maintain the gain in such a way that the peak of the signal in the QRS complex just meets the AGC target, as shown in FIG. 3.

In order to appropriately control the heart, a dual chambered pacemaker should not only control the gain of its sensors, but it should also enable and disable at appropriate times. Both the atrial sense amplifier 80 and the ventricular sense amplifier 85 have appropriate pacemaker refractory periods to avoid cross-talk between the chambers. The basic pacemaker refractory period for one chamber of the heart, according to the teachings of my invention, should be set based on the magnitude of the output pulse in the other chamber of the heart, and the gain of sense amplifier in the selected chamber of the heart. For example, if the ventricular blanking period resulting from an atrial pace is to be determined, the amount of energy in the atrial output pulse from the atrial stimulus generator 75 and the gain of the ventricular sense amplifier 85 should be determined by the microprocessor 50 and the length of the ventricular blanking period should be adjusted in accordance with the set values of the two parameters.

Figure 5:
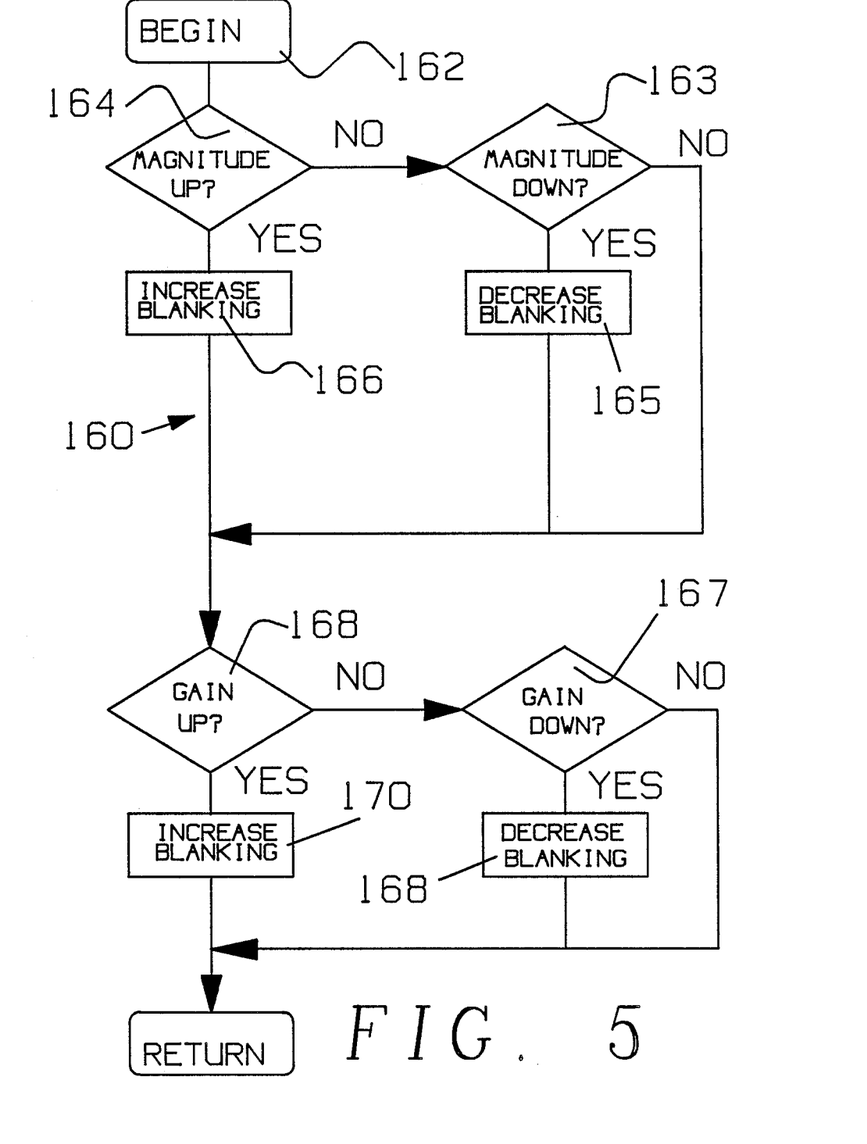
FIG. 5 is a flow chart for adjusting a blanking refractory period for implementation with the pacemaker of FIG. 1.

As shown in FIG. 5, the preferred implementation of my invention comprises a subroutine 160 implemented on the microprocessor 50. When the subroutine is invoked 162 the microprocessor 50 interrogates 164 the appropriate stimulus generator, for example, stimulus generator 75, and determines the current preferred magnitude of output for the stimulus generator. In a dynamic DDD pacemaker such as the one described herein, the output magnitude of the stimulus generator is continually updated, based on current conditions to minimize the effective magnitude of the output pulse. If the pulse magnitude has increased, the microprocessor 50 would increase 166 the blanking period. In the preferred embodiment, an increase of 10 microjoules might cause an increase of 10 milliseconds in the blanking period.

If the pulse magnitude has decreased 163, to the microprocessor 50 would decrease 165 the refractory period. The microprocessor 50 then interrogates 168 a sense amplifier, for example, the ventricular sense amplifier 85 if the blanking period were being determined. If the ventricular gain had increased, the microprocessor 50 would increase 170 the blanking period. A step increase/decrease or other function could be implemented. For example, if the microprocessor 50 determines that the sensitivity was greater than 1.8 millivolts, 15 milliseconds might be added to the refractory period. If the sensitivity of the sense amplifier had decreased 167, the microprocessor would decrease 169 the blanking period.

In a DDD pacemaker, the atrial sense amplifier 80 should also be controlled to permit true Wenckebach behavior in situations where the ventricle is being paced at the maximum pacing rate. This behavior can be understood with reference to first graph 172 in FIG. 4. In the first graph 172 a high atrial rate, represented by the small pulses, is illustrated. The pulses in the ventricle, shown as large pulses in the first graph 172, are paced at the maximum ventricle rate and therefor are evenly spaced 174 in time. After each ventricular pulse there is an atrial pacemaker refractory period 176. Because the ventricle is paced at a constant rate, the elapsed time 178 between an atrial pulse and its associated ventricular pulse gradually increases until an atrial pulse 180 falls within the atrial pacemaker refractory period and is not detected in the atrium. When this occurs, the ventricle will not be stimulated until after the next detected atrial event 182. There will be a missed beat in the ventricle, resulting in a so-called Wenckebach pause. The next ventricular beat 184, however, will again be synchronized with its preceding atrial beat 182.

Figure 4:
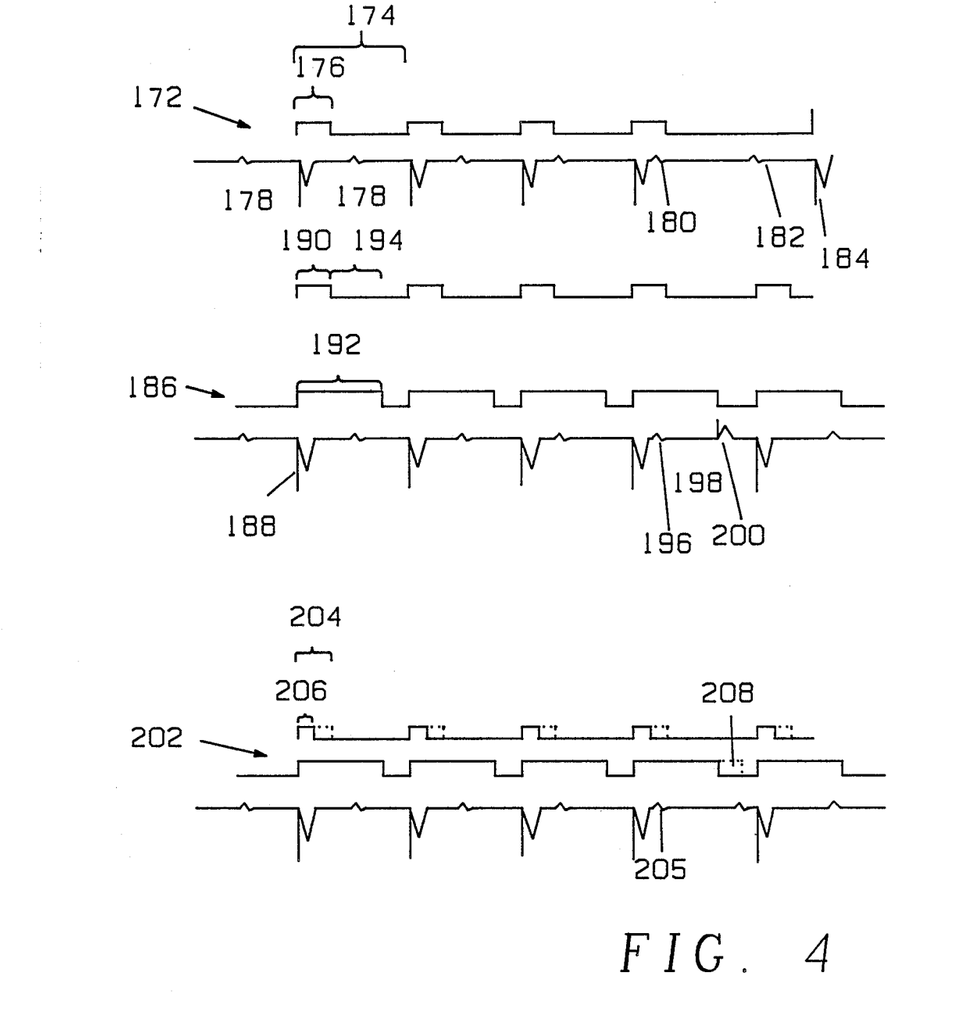
FIG. 4 is a set of graphs showing relative interaction of a paced heart and the pacemaker of FIG. 1.

In DDD pacemakers which permit high programmed pacing rates or are rate responsive, however, a situation may occur such as the one shown in a second graph 186 of FIG. 4. As seen in the second graph 186, a ventricular pulse 188 is followed by an atrial pacemaker refractory period 190. The pacemaker sets an interval 192, called the V-A delay, during which an atrial event must be sensed or the pacemaker will stimulate the atrium. Because of the atrial pacemaker refractory period 190 the atrial event can only be sensed during a short window 194. At high pacing rates, or with a rate adaptive DDD pacemaker, it is possible for an atrial event 196 to occur during an atrial pacemaker refractory period, initiating a Wenckebach pause, but to have the next naturally occurring atrial pulse fall outside the window 194. The pacemaker would be then committed to pace 200 the atrium. In this situation, atrial-ventricular synchrony may not be achieved. The atrium could actually be accelerated to a still higher rate or retrograde conduction to the atrium could occur after the ventricular paced beat. Any of these conditions is to be avoided if possible.

One means of avoiding an inappropriate atrial pace during a Wenckebach pause is to lengthen the V-A delay 192 whenever the ventricle is paced at maximum ventricular rate. If pacing rate is the only criteria, however, a premature atrial contraction can cause a momentary ventricular pacing rate equal to the maximum ventricular pacing rate. Thereafter, the V-A delay would be inappropriately lengthened. In addition, sensing atrial noise may cause a similar condition.

To avoid these conditions, I have provided for conditional sensing during relative atrial pacemaker refractory periods. As shown in a third graph 202 of FIG. 4, a relative pacemaker refractory period 204 continues after the atrial sense amplifier 80 is enabled after a preselected time 206. If an atrial event is detected during the relative atrial pacemaker refractory period 204, this is an indication that true Wenckebach behavior has been detected. The ventricle is not paced, and, provided the ventricle is being paced at the maximum ventricular rate, the V-A delay is extended 208.

Figure 6:
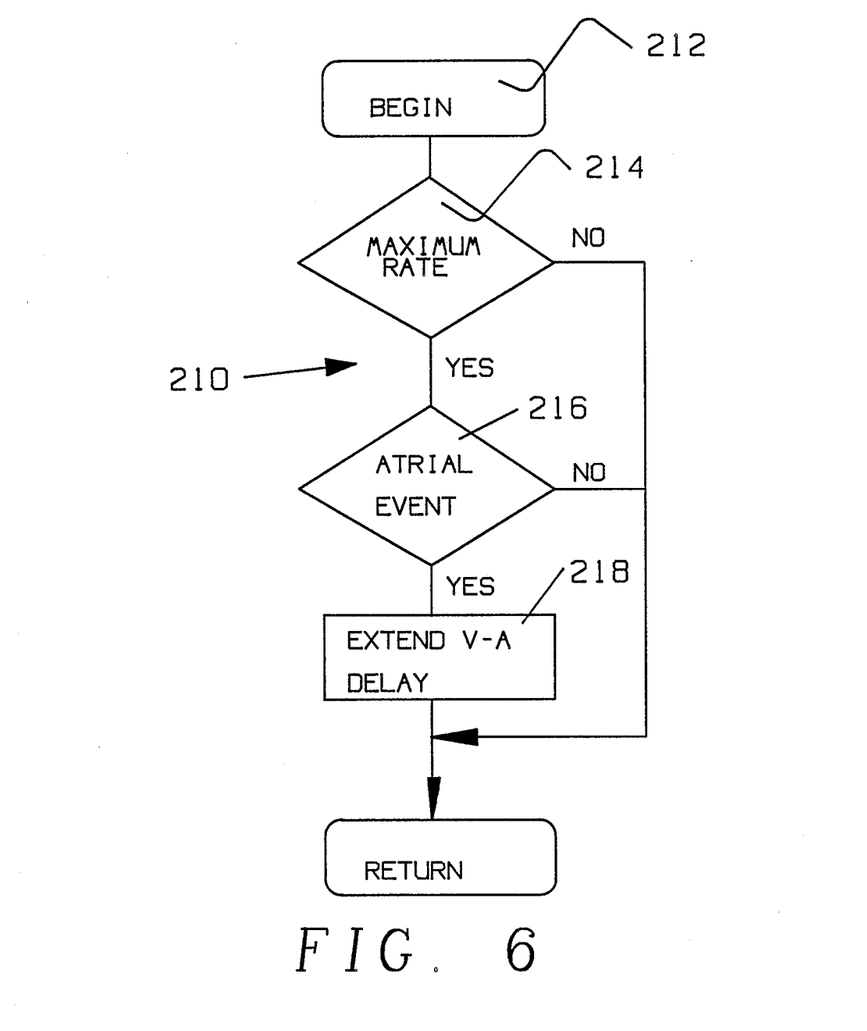
FIG. 6 is a flow chart for increasing a V-A delay period.

In the preferred embodiment, this is implemented by subroutine 210 of FIG. 6. When the subroutine 210 is invoked 212, the microprocessor 50 determines 214 if the ventricle is being paced at the maximum ventricular rate. If this condition is met, the microprocessor 50 checks 216 if a atrial event 205 has been detected during the relative atrial pacemaker refractory period 204. If both conditions are met, the V-A delay period is extended 218 for one cycle so that an actual Wenckebach pause can occur and atrial ventricular synchrony can be restored.

My invention may be embodied in other specific forms without departing from the spirit or essential characteristics thereof. The present embodiment is therefore considered in all respects to be illustrative and not restrictive, the scope of my invention being indicated by the appended claims rather than by the foregoing description and all changes which come within the meaning and range of equivalency of the claims are therefor intended to be embraced therein.

I claim as my invention:

1. A dual chamber cardiac pacemaker comprising means for detecting a maximum ventricular heart rate, means for detecting an atrial event during a relative atrial refractory period, and means responsive to the heart rate detecting means and to the atrial event detecting means for extending a ventricular-atrial delay period.

2. A cardiac pacemaker according to claim 1 wherein the atrial event detecting means further, comprises at least one sense amplifier adapted to be in electrical communication with an atrial chamber of a paced heart, means for disabling the sense amplifier upon the occurrence of a ventricular event, means for enabling the sense amplifier after a first period of time, and means for responding to an atrial event during a second period of time following said first period of time.

3. A cardiac pacemaker according to claim 2 wherein the heart rate detecting means further comprises means for pacing the heart at a selected maximum rate and means for recognizing if the pacemaker is stimulating the heart at the selected maximum rate.

4. A cardiac pacemaker according to claim 3 wherein the delay period extending means further comprises means for lengthening the delay period for a selected number of cardiac cycles.

5. A cardiac pacemaker according to claim 4 wherein the delay lengthening means comprises means for lengthening the delay period for one cycle.

6. A cardiac pacemaker according to claim 5 further comprising means for delivering pulses to at least a first chamber of the heart means for determining the magnitude of pulses delivered by the pacemaker to the first chamber of the heart, amplifier means for sensing events in a second chamber of the heart, means for determining gain of the amplifier means and means responsive to the magnitude determining means and to the gain determining means for adjusting a blanking period of the amplifier means for the second chamber of the heart.

7. The cardiac pacemaker of claim 6 wherein the blanking period adjusting means further comprises first means responsive to the magnitude determining means for making a first adjustment to the blanking period, and second means responsive to the gain determining means for making a second adjustment to the blanking period.

8. The cardiac pacemaker of claim 7 wherein the first responsive means further comprises means for increasing the blanking period if the magnitude of pulses has increased and means for decreasing the blanking period if the magnitude of pulses has decreased and wherein the second responsive means further comprises means for increasing the blanking period if the gain has increased and means for decreasing the blanking period if the gain has decreased.

9. The cardiac pacemaker according to claim 8 wherein the pulse delivering means comprise means for delivering pulses to a atrial chamber of the heart and wherein the amplifier means comprise means for sensing events in a ventricular chamber of the heart.

10. The cardiac pacemaker of claim 9 further comprising means for delivering pulses to the ventricular chamber of the heart, means for determining the magnitude of pulses delivered by the pacemaker to the ventricular chamber of the heart, amplifier means for sensing events in the atrial chamber of the heart, means for determining gain of the artrial amplifier means and means responsive to the magnitude determining means and to the gain determining means for adjusting a blanking period of the amplifier means for the artrial chamber of the heart.

11. A dual chamber cardiac pacemaker comprising means for delivering pulses to at least a first chamber of the heart, means for determining the magnitude of pulses delivered by the pacemaker to the first chamber of the heart, amplifier means for sensing events in a second chamber of the heart, means for determining gain of the amplifier means, and means responsive to the magnitude determining means and to the gain determining means for adjusting a blanking period of the amplifier means for the second chamber of the heart, said blanking period adjusting means further comprising first means responsive to the magnitude determining means for making a first adjustment to the blanking period, and second means responsive to the gain determining means for making a second adjustment to the blanking period.

12. The cardiac pacemaker of claim 11 wherein the first responsive means further comprises means for increasing the blanking period if the magnitude of pulses has increased and means for decreasing the blanking period if the magnitude of pulses has decreased and wherein the second responsive means further comprises means for increasing the blanking period if the gain has increased and means for decreasing the blanking period if the gain has decreased.

13. The cardiac pacemaker according to claim 12 wherein the pulse delivering means comprise means for delivering pulses to an atrial chamber of the heart and wherein the amplifier means comprise means for sensing events in a ventricular chamber of the heart.

14. The cardiac pacemaker of claim 13 further comprising means for delivering pulses to the ventricular chamber of the heart means for determining the magnitude of pulses delivered by the pacemaker to the ventricular chamber of the heart, amplifier means for sensing events in the atrial chamber of the heart, means for determining gain of the atrial amplifier means and means responsive to the magnitude determining means and to the gain determining means for adjusting a blanking period of the amplifier means for the atrial chamber of the heart.

15. The cardiac pacemaker according to claim 14 further comprising means for detecting a maximum a ventricular heart rate, means for detecting an atrial event during a relative atrial refractory period, and means responsive to the heart rate detecting means and to the atrial event detecting means for extending a ventricul-aratrial delay period.

16. A cardiac pacemaker according to claim 15 wherein the atrial event detecting means further comprise at least one sense amplifier adapted to be in electrical communication with an atrial chamber of a paced heart, means for disabling the sense amplifier upon the occurrence of a ventricular event, means for enabling the sense amplifier after a first period of time, and means for responding to an atrial event during a second period of time following said first period of time.

17. A cardiac pacemaker according to claim 16 wherein the rate detecting means further comprises means for pacing the heart at a selected maximum rate and means for recognizing if the pacemaker is stimulating the heart at the selected maximum rate.

18. A cardiac pacemaker according to claim 17 wherein the delay period extending means further comprises means for lengthening the delay period for a selected number of cardiac cycles.

19. A cardiac pacemaker according to claim 18 wherein the delay lengthening means comprises means for lengthening the delay period for one cycle.

* * * * *